US012781287B2

(12) United States Patent
Zhao et al.

(10) Patent No.: US 12,781,287 B2
(45) Date of Patent: Nov. 3, 2026

(54) INSTANT NUCLEIC ACID TEST METHOD AND TEST KIT FOR PATHOGENIC MUTANTS

(71) Applicant: Shenzhen Institute of Advanced Technology, Chinese Academy of Sciences, Shenzhen (CN)

(72) Inventors: Wei Zhao, Shenzhen (CN); Guiyue Tang, Shenzhen (CN); Wei Tan, Shenzhen (CN); Guoping Zhao, Shenzhen (CN)

(73) Assignee: Shenzhen Institute of Advanced Technology, Chinese Academy of Sciences, Shenzhen (CN)

( * ) Notice: Subject to any disclaimer, the term of this patent is extended or adjusted under 35 U.S.C. 154(b) by 952 days.

(21) Appl. No.: 18/085,637

(22) Filed: Dec. 21, 2022

(65) Prior Publication Data

US 2024/0002958 A1 Jan. 4, 2024

(30) Foreign Application Priority Data

Jun. 9, 2022 (CN) ......................... 202210644033.4

(51) Int. Cl.
*C12Q 1/70* (2006.01)

(52) U.S. Cl.
CPC ....... *C12Q 1/701* (2013.01); *C12Q 2600/156* (2013.01)

(58) Field of Classification Search
CPC .......................... C12Q 2600/156; C12Q 1/701
See application file for complete search history.

(56) References Cited

FOREIGN PATENT DOCUMENTS

| | | | | | |
|---|---|---|---|---|---|
| CN | 112501353 A | | 3/2021 | | |
| CN | 113215164 | | 8/2021 | | |
| CN | 114045356 A | | 2/2022 | | |
| CN | 114107567 A | | 3/2022 | | |
| CN | 113215164 B | * | 6/2022 | ......... | C12N 15/1131 |
| KR | 20210119256 A | * | 10/2021 | ............. | C12Q 1/701 |

OTHER PUBLICATIONS

Tang et al., (medRxiv, doi.org/10.1101/2022.05.11.22274884; published May 16, 2022) (Year: 2022).*
Lin et al., (Food and Agricultural Immunology, vol. 31, p. 447-462; published 2020 ). (Year: 2020).*
Zhang et al. (Frontiers in Bioengineering and Biotechnology; vol. 10:866368. Doi: 10.3389/fbioe.2022.866368; published May 3, 2022) (Year: 2022).*
Tang et al., (medRxiv, doi.org/10.1101/2022.05.11.22274884; published May 16, 2022) (Year: 2022), Supplementary Materials (Year: 2022).*

* cited by examiner

*Primary Examiner* — Robert B Mondesi
*Assistant Examiner* — George Themistoclis Lountos
(74) *Attorney, Agent, or Firm* — Menachem Nathan; Nathan & Associates

(57) ABSTRACT

The present disclosure discloses an instant nucleic acid detection method and detection kit for detecting pathogenic mutants, belongs to the technical field of biological detection, includes the following steps: Step 1): collecting samples, and extracting sample nucleic acids; Step 2): designing crRNA used in a CRISPR process, selecting Cas9 nuclease, Cas13 nuclease or Cas12a nuclease; and Step 3): detecting the sample nucleic acids by using the CRISPR process combined with a colloidal gold test paper method or a fluorescence signal detection method.

10 Claims, 7 Drawing Sheets

Specification includes a Sequence Listing.

```
                              SEQUENCE LISTING


Sequence total quantity: 17
SEQ ID NO: 1            moltype = DNA  length = 30
FEATURE                 Location/Qualifiers
source                  1..30
                        mol_type = other DNA
                        organism = synthetic construct
SEQUENCE: 1
gaagagacag gtacgttaat agttaatagc                                   30

SEQ ID NO: 2            moltype = DNA  length = 34
FEATURE                 Location/Qualifiers
source                  1..34
                        mol_type = other DNA
                        organism = synthetic construct
SEQUENCE: 2
cagattttta acacgagagt aaacgtaaaa agaa                              34

SEQ ID NO: 3            moltype = DNA  length = 31
FEATURE                 Location/Qualifiers
source                  1..31
                        mol_type = other DNA
                        organism = synthetic construct
SEQUENCE: 3
tgtatagatt gtttaggaag tctaatctca a                                 31

SEQ ID NO: 4            moltype = DNA  length = 30
FEATURE                 Location/Qualifiers
source                  1..30
                        mol_type = other DNA
                        organism = synthetic construct
SEQUENCE: 4
agactcagta agaacacctg tgcctgttaa                                   30

SEQ ID NO: 5            moltype = DNA  length = 33
FEATURE                 Location/Qualifiers
source                  1..33
                        mol_type = other DNA
                        organism = synthetic construct
SEQUENCE: 5
accagatgat tttacaggct gcgttatagc ttg                               33

SEQ ID NO: 6            moltype = DNA  length = 27
FEATURE                 Location/Qualifiers
source                  1..27
                        mol_type = other DNA
                        organism = synthetic construct
SEQUENCE: 6
caattaaaac ctttaacacc attacaa                                      27

SEQ ID NO: 7            moltype = DNA  length = 32
FEATURE                 Location/Qualifiers
source                  1..32
                        mol_type = other DNA
                        organism = synthetic construct
SEQUENCE: 7
tttccaatgt tacttggttc catgtttact at                                32

SEQ ID NO: 8            moltype = DNA  length = 32
FEATURE                 Location/Qualifiers
source                  1..32
                        mol_type = other DNA
                        organism = synthetic construct
SEQUENCE: 8
ttaacaataa gtagggactg ggtcttcgaa tc                                32

SEQ ID NO: 9            moltype = DNA  length = 20
FEATURE                 Location/Qualifiers
source                  1..20
                        mol_type = other DNA
                        organism = synthetic construct
SEQUENCE: 9
gattagcgta cgcacgttac                                              20
```

-continued

```
SEQ ID NO: 10          moltype =   length =
SEQUENCE: 10
000

SEQ ID NO: 11          moltype = RNA  length = 37
FEATURE                Location/Qualifiers
source                 1..37
                       mol_type = other RNA
                       organism = synthetic construct
SEQUENCE: 11
aatttctact gttgtagatc aagactcacg ttaacaa                          37

SEQ ID NO: 12          moltype = RNA  length = 36
FEATURE                Location/Qualifiers
source                 1..36
                       mol_type = other RNA
                       organism = synthetic construct
SEQUENCE: 12
aatttctact gttgtagatc aacccactaa tggtgt                           36

SEQ ID NO: 13          moltype = RNA  length = 36
FEATURE                Location/Qualifiers
source                 1..36
                       mol_type = other RNA
                       organism = synthetic construct
SEQUENCE: 13
aatttctact gttgtagatc aacccactta tggtgt                           36

SEQ ID NO: 14          moltype = RNA  length = 36
FEATURE                Location/Qualifiers
source                 1..36
                       mol_type = other RNA
                       organism = synthetic construct
SEQUENCE: 14
aatttctact gttgtagatc tatacatgtc tctggg                           36

SEQ ID NO: 15          moltype = RNA  length = 36
FEATURE                Location/Qualifiers
source                 1..36
                       mol_type = other RNA
                       organism = synthetic construct
SEQUENCE: 15
aatttctact gttgtagatc tatctctggg accaat                           36

SEQ ID NO: 16          moltype = RNA  length = 36
FEATURE                Location/Qualifiers
source                 1..36
                       mol_type = other RNA
                       organism = synthetic construct
SEQUENCE: 16
aatttctact gttgtagatt gtggtaatgt tccaca                           36

SEQ ID NO: 17          moltype = RNA  length = 36
FEATURE                Location/Qualifiers
source                 1..36
                       mol_type = other RNA
                       organism = synthetic construct
SEQUENCE: 17
aatttctact gttgtagatt gtggtaatgt tccaaa                           36
```

INSTANT NUCLEIC ACID TEST METHOD AND TEST KIT FOR PATHOGENIC MUTANTS

CROSS-REFERENCE TO RELATED APPLICATIONS

The present application is based upon and claims priority to Chinese Patent Application No. 202210644033.4, filed on Jun. 9, 2022, the entire content thereof is incorporated herein by reference.

STATEMENT REGARDING SEQUENCE LISTING

The instant application contains a Sequence Listing which has been submitted in XML format via USPTO Patent Center and is hereby incorporated by reference in its entirety. Said XML copy, created on Oct. 12, 2022, is named SIAT-0902 US Sequence_listing.xml.xml and is 15,100 bytes in size.

TECHNICAL FIELD

The present disclosure belongs to the technical field of biological detection, and relates to a detection method and detection kit for detecting pathogenic mutants.

BACKGROUND

Pathogens of infectious diseases, especially viruses, are easily mutated during the propagation due to their lacks of replication inspection and damage repair mechanisms. By taking novel coronavirus as an example, since November 2020, the World Health Organization has issued 5 widely prevalent SARS-CoV-2 variants, namely Alpha, Beta, Gamma, Delta and Omicron (Munnink B B O, Sikkema R S, Nieuwenhuijse D F, Molenaar R J, Munger E, Molenkamp R, et al. *Transmission of SARS-CoV-2 on mink farms between humans and mink and back to humans. Science.* 2021; 371(6525): 172-7), which are designated as "closely watched mutants".

Nucleic acid-based pathogen detection has become a gold standard for diagnosing pathogen infection. Reverse transcription real-time quantitative PCR (RT-qPCR), as a typical nucleic acid detection technology, transforms a target virus RNA into cDNA through reverse transcription, and then cDNA is subjected to PCR amplification in combination with real-time fluorescence detection, so as to sensitively and accurately quantify RNA viruses in a sample (Feng W, Newbigging A M, Le C, Pang B, Peng H Y, Cao Y R, et al. *Molecular Diagnosis of COVID-19: Challenges and Research Needs. Anal Chem.* 2020; 92(15): 10196-209). However, since RT-qPCR is an amplicon-based detection method, it is not applicable to genetic typing of SARS-CoV-2 mutants. A recent study shows that multiplex qPCR can be used to distinguish some SARS-CoV-2 mutants by targeting specific small deletions (Chung H Y, Jian M J, Chang C K, Lin J C, Yeh K M, Chen C W, et al. *Emergency SARS-CoV-2 variants of Concern: Novel Multiplex Real-Time RT-PCR Assay for Rapid Detection and Surveillance. Microbiol Spectr.* 2022; 10(1)). However, such the method is not sensitive to unit point mutation of SARS-CoV-2. At present, detection methods of SARS-CoV-2 mutants mainly based on whole genome sequencing. However, whole genome sequencing not only depends on lots of instruments and well-trained personnel, but also is time-consuming and relatively high in cost (Arena F, Pollini S, Rossolini G M, Margaglione M. *Summary of the Available Molecular Methods for Detection of SARS-CoV-2 during the Ongoing Pandemic. Int J Mol Sci.* 2021; 22(3). Epub 2021/02/03).

Therefore, there are different drawbacks (low applicability, low sensitivity, long time consumption, high cost, dependence on equipment and instruments, etc.) for the current detection methods of pathogenic mutants. Hence, there is a lack of a rapid, sensitive and accurate detection method for pathogenic mutants.

SUMMARY

In view of the problems of low applicability, low sensitivity, long time consumption, high cost, dependence on equipment and instruments and the like existing in the current detection methods of pathogenic mutants, the present disclosure provides an instant nucleic acid detection method and detection kit for pathogenic mutants, so as to achieve the purpose of rapidly, sensitively and accurately detecting pathogenic mutants.

The present disclosure provides an instant nucleic acid detection method for pathogenic mutants, comprising the following steps:

Step 1): collecting samples, and extracting sample nucleic acids;

Step 2): designing crRNA for a CRISPR process, selecting Cas9 nuclease, Cas13 nuclease or Cas12a nuclease as a Cas protein used in the CRISPR process; and Step 3): detecting the sample nucleic acids by using the CRISPR process combined with a colloidal gold test paper method or a fluorescence signal detection method.

The CRISPR process is an efficient gene editing tool. crRNA (guide RNA) is a guide RNA, which is capable of guiding the Cas protein specifically binding to a target DNA fragment (the nucleic acid obtained by Step 1)). When the target DNA fragment binds to the Cas protein and crRNA in a CRISPR system to form a ternary complex, the trans-cleavage activity of the Cas protein is activated; when there is no target DNA fragment, the ternary complex cannot be formed, thereby not able to activate the trans-cleavage activity of the Cas protein. Based on the above difference, recognition of mutation points of pathogens is realized, and then pathogenic mutants are detected by combining with the colloidal gold test paper method or fluorescence signal detection method. The CRISPR process provides starting detection samples for subsequent detection using the colloidal gold test paper method or fluorescence signal detection method after specifically amplifying conventional detected signals, can accurately distinguish negative samples from positive samples and greatly increase the sensitivity of the detection method. Meanwhile, by integrating the instant and rapid advantages of the colloidal gold test paper method or fluorescence signal detection method, a purpose of rapidly, sensitively and accurately detecting the pathogenic mutants is realized.

Further, the method for extracting sample nucleic acids in Step 1) is to use a sample lysate, and specifically comprises the following steps: lysing the sample in the sample lysate to directly release nucleic acid without extraction and purification of the sample nucleic acid, thereby greatly simplifying the step of extracting nucleic acid, shortening the time of the whole detection and improving the detection efficiency, which is more conducive to rapid detection.

Further, when the sample nucleic acid extracted in Step 1) is RNA, extracted RNA undergoes RT reaction to obtain DNA; when the sample nucleic acid extracted in Step 1) is DNA, DNA is directly used for subsequent steps, as such, this detection method is applicable to pathogens of different nucleic acids, thereby improving the applicability of this detection method.

Further, this detection method also comprises Step 11). The Step 11) is to amplify obtained DNA by RPA reaction or LAMP reaction to realize signal enlargement, recombinase polymerase (RPA) or LAMP (loop-mediated isothermal amplification) can increase the amount of trace nucleic acid extracted from the sample, thereby increasing the sensitivity of this detection method.

Further, the Cas protein used in the CRISPR process is Cas12a nuclease, which has higher site recognition specificity relative to Cas9 nuclease or Cas13 nuclease to further improve the specificity of this detection method, thereby further improving the accuracy of the detection result.

Further, the crRNA designed in Step 2) includes crRNA_wild type and crRNA_mutant type, the crRNA_wild type is for unmutated pathogens and binds to unmutated sample nucleic acid, the crRNA_mutation type is for mutated pathogens and binds to mutated sample nucleic acid, and the target DNA is respectively detected through the crRNA_wild type and the crRNA_mutant type so as to distinguish whether pathogens are mutant strains.

The present disclosure also provides an instant nucleic acid detection kit of pathogenic mutants, comprising a Cas protein, colloidal gold test paper and a colloidal gold probe, wherein the colloidal gold test paper includes a C tape and a T tape, the colloidal gold probe includes a first probe sequence as well as a conjugate A and a conjugate B that are respectively connected with two ends of the first probe sequence, the C tape is provided with an antibody A binding to the conjugate A, and the T tape is provided with an antibody B binding to the conjugate B. The colloidal gold probe is used for combining the CRISPR process with the colloidal gold test paper method to detecting the sample nucleic acids in the abovementioned instant nucleic acid detection method of the pathogenic mutants;

when the sample contains target DNA and when the target DNA fragment binds to the Cas protein and crRNA in the CRISPR system to form the ternary complex, the trans-cleavage activity of the Cas protein is activated, the Cas protein cleaves the first probe sequence so that when the colloidal gold probe flows to the C tape, the conjugate A binds to the antibody A to produce color, and when the colloidal gold probe flows to the T tape, the conjugate B binds to the antibody B to produce color, thus the result is positive; when there is no target DNA fragment, the ternary complex cannot be formed, thereby not able to activate the trans-cleavage activity of the Cas protein, the colloidal gold probe can only flow to the C tape to bind to the antibody A to produce color, but cannot flow to the T tape, thus the result is negative, thereby realizing the purpose of rapidly detecting and achieving the visual reading of the detection result without depending on equipment and instruments so as to really realize the instant detection.

And/or, the instant nucleic acid detection kit includes the Cas protein and a fluorescent probe, the fluorescent probe includes a second probe sequence as well as a fluorophore and a quenching group that are respectively labeled at two ends of the second probe sequence, and is used for combining with the CRISPR process to detecting the sample nucleic acids in the abovementioned instant nucleic acid detection method of the pathogenic mutants, in like manner, if the target DNA fragment is present, the second probe sequence is correspondingly cleaved to emit light, otherwise, light is not emitted. The fluorescent value is detected using ELIASA, so as to correspondingly realize the purpose of detecting the pathogenic mutants.

Further, the conjugate A is biotin which is conjugated with streptavidin, the conjugate B is fluorescein isothiocyanate, the antibody A is an anti-streptavidin antibody, the antibody B is an anti-fluorescein isothiocyanate antibody, and the first probe sequence is cleaved. When the colloidal gold probe flows to the C tape, streptavidin conjugated with biotin binds to the anti-streptavidin antibody and is color developed on the C tape; when the colloidal gold probe flows to the T tape, the fluorescein isothiocyanate binds to the anti-fluorescein isothiocyanate antibody to produce color, and the result is positive; the first probe sequence is not cleaved, the colloidal gold probe can only flow to the C tape to produce color but cannot flow to the T tape and cannot be color developed on the T tape, and the result is negative; if no color developing on the C tape, it indicates that the test paper itself has a quality problem, as such, the purposes of rapid detection and visual reading of the detection result are realized.

Further, when the pathogen is novel coronavirus, the novel coronavirus includes E gene, S gene 501 site, S gene 478 site and S gene H69-V70 site, the first probe sequence is as shown in SEQ ID NO. 9, the second probe sequence is as shown in SEQ ID NO. 10, the kit also includes a forward RT-RPA primer and a reverse RT-RPA primer, the sequence of the forward RT-RPA primer is as shown in SEQ ID NO. 1, and the sequence of the reverse RT-RPA primer is as shown in SEQ ID NO. 2 and used for detecting the E gene;

and/or, the sequence of the forward RT-RPA primer is as shown in SEQ ID NO. 3, and the sequence of the reverse RT-RPA primer is as shown in SEQ ID NO. 4 and used for detecting the S gene 501 site;

and/or, the sequence of the forward RT-RPA primer is as shown in SEQ ID NO. and the sequence of the reverse RT-RPA primer is as shown in SEQ ID NO. 6 and used for detecting the S gene 478 site;

and/or, the sequence of the forward RT-RPA primer is as shown in SEQ ID NO. 7, and the sequence of the reverse RT-RPA primer is as shown in SEQ ID NO. 8.

Further, the kit also includes a crRNA sequence which is crRNA-E for E gene, and the sequence of crRNA-E is as shown in SEQ ID NO. 11;

and/or, the crRNA sequences are crRNA-N501 and crRNA-Y501 for S gene 501 site, the sequence of crRNA-N501 is as shown in SEQ ID NO. 12, and the sequence of crRNA-N501 is as shown in SEQ ID NO. 13;

and/or, the crRNA sequences are crRNA-H69-V70 and crRNA-ΔH69-V70 for S gene H69-V70 site, the sequence of crRNA-H69-V70 is as shown in SEQ ID NO. 14, and the sequence of crRNA-ΔH69-V70 is as shown in SEQ ID NO. 15;

and/or, the crRNA sequences are crRNA-T478 and crRNA-K478 for S gene 478 site, the sequence of crRNA-T478 is as shown in SEQ ID NO. 16, and the sequence of crRNA-K478 is as shown in SEQ ID NO. 17.

By selecting the above detection sites and correspondingly designing crRNA, the purpose of detecting the novel coronavirus (SARS-CoV-2) mutant can be realized.

Compared with the related art, the present disclosure has the beneficial effects:

the present disclosure combines the CRISPR process with the instant detection method, the CRISPR process provides the starting detection sample for detection with the subsequent instant detection method after specifically amplifying conventional detected signal, is capable of accurately distinguishing negative samples from positive samples, thereby greatly increasing the sensitivity of the detection method and realizing the purposes of rapidly, sensitively and accurately detecting virus mutants. Combination of the CRISPR process with the colloidal gold test paper detection process realizes the visual reading of the detection result. The CRISPR process selects Cas12a which has higher site recognition specificity relative to Cas9 or Cas13, the recognition of point mutation in SARS-CoV-2 is realized by designing specific crRNA, and the detection method of the present disclosure has the advantages of high sensitivity and high specificity by combining with a RPA amplification technology (when nucleic acid is RNA, RT reaction is first carried out). Furthermore, the present disclosure utilizes specific virus lysate to realize the direct release of SARS-CoV-2 virus nucleic acid and seamless connection of subsequent amplification and detection steps. The present disclosure avoids dependency on equipment and instruments, thereby truly realizing instant detection, can rapidly and accurately detect pathogenic mutation, and can be used applied to people's self-inspection and places such as hospitals to detect infectious disease pathogens (such as SARS-CoV-2) and their mutants.

BRIEF DESCRIPTION OF THE DRAWINGS

For a better understanding of the aforementioned embodiments of the invention as well as additional embodiments thereof, reference should be made to the Description of Embodiments below, in conjunction with the following drawings in which like reference numerals refer to corresponding parts throughout the figures.

DETAILED DESCRIPTION OF THE EMBODIMENTS

Figure 1A:
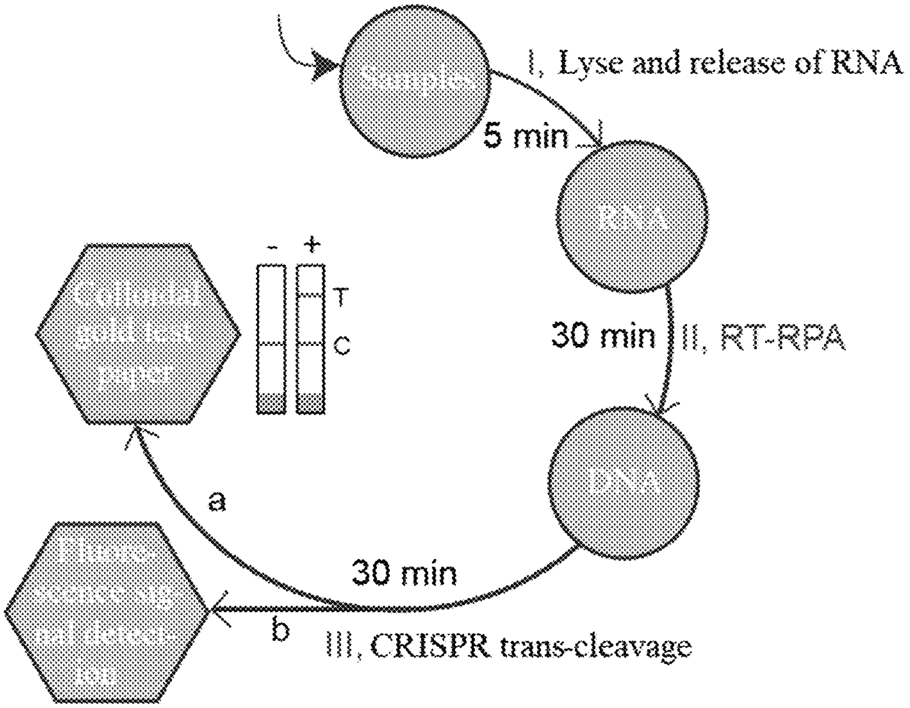
FIG. 1A is a technology roadmap for nucleic acid detection of novel coronavirus mutants.

For more clearly understanding the technical problem, technical solution and beneficial effects of the present disclosure, the present disclosure will be further described in detail in combination with drawings and examples. It should be understood that specific embodiments described herein are only for explaining the present disclosure but not limiting the present disclosure.

The embodiments of the present disclosure provides an instant nucleic acid detection method for pathogenic mutants, comprising the following steps:

Step 1): collecting samples, and extracting sample nucleic acids;

Step 2): designing crRNA used in a CRISPR process, selecting Cas9 nuclease, Cas13 nuclease or Cas12a nuclease as a Cas protein used in the CRISPR process; and Step 3): detecting sample nucleic acids by using the CRISPR process combined with a colloidal gold test paper method or fluorescence signal detection method.

The CRISPR process is an efficient gene editing tool, crRNA (guide RNA) is a guide RNA which is capable of guiding the Cas protein specifically binding to a target DNA fragment (the nucleic acid obtained by Step 1)). When target DNA binds to the Cas protein and crRNA in a CRISPR system to form a ternary complex, the trans-cleavage activity of the Cas protein is activated; when there is no target DNA fragment, the ternary complex cannot be formed, thereby not able to activate the trans-cleavage activity of the Cas protein. Based on the above difference, recognition of mutation points of pathogens is realized, and then pathogenic mutants are detected by combining with the colloidal gold test paper method or fluorescence signal detection method. The CRISPR process provides starting detection samples for the subsequent detection using the colloidal gold test paper method or fluorescence signal detection method after amplifying specifically conventional detected signals, and can accurately distinguish negative samples from positive samples so as to greatly increase the sensitivity of the detection method. Meanwhile, by integrating the instant and rapid advantages of the colloidal gold test paper method or the fluorescence signal detection method, a purpose of rapidly, sensitively and accurately detecting the pathogenic mutants is realized.

Specifically, the method for extracting sample nucleic acid in Step 1) is to use a sample lysate, and specifically comprises the following steps: lysing the sample in the sample lysate to directly release nucleic acid without extraction and purification of sample nucleic acid, thereby greatly simplifying the step of extracting nucleic acid, shortening the time of the whole detection and improving the detection efficiency, which is more conducive to rapid detection.

Specifically, when the sample nucleic acid extracted in Step 1) is RNA, extracted RNA undergoes RT reaction to obtain DNA; when the sample nucleic acid extracted in Step 1) is DNA, DNA is directly used for subsequent steps, as such, this detection method is applicable to pathogens of different nucleic acids, thereby improving the applicability of this detection method.

Specifically, this detection method also comprises Step 11). The Step 11) is to amplify obtained DNA by RPA reaction or LAMP reaction to realize signal enlargement, recombinase polymerase (RPA) or LAMP (loop-mediated isothermal amplification) can increase the amount of trace nucleic acid extracted from the sample, thereby increasing the sensitivity of this detection method.

Specifically, the Cas protein used in the CRISPR process is Cas12a nuclease, which has higher site recognition specificity relative to Cas9 nuclease or Cas13 nuclease to further improve the specificity of this detection method, thereby further improving the accuracy of the detection result.

Specifically, crRNA designed in Step 2) includes crRNA_wild type and crRNA_mutant type, the crRNA_wild type is for unmutated pathogens and binds to unmutated sample nucleic acid, the crRNA_mutation type is for mutated pathogens and binds to mutated sample nucleic acid, the target DNA is respectively detected through the crRNA_wild type and the crRNA_mutant type so as to distinguish whether pathogens are mutant strains.

The embodiments of the present disclosure also provide an instant nucleic acid detection kit of pathogenic mutants, comprising a Cas protein, colloidal gold test paper and a colloidal gold probe, wherein the colloidal gold test paper includes a C tape and a T tape, the colloidal gold probe includes a first probe sequence as well as a conjugate A and a conjugate B that are respectively connected with two ends of the first probe sequence, the C tape is provided with an antibody A binding to the conjugate A, and the T tape is provided with an antibody B binding to the conjugate B. The colloidal gold probe is used for combining the CRISPR process with the colloidal gold test paper method to detecting the sample nucleic acids in the abovementioned instant nucleic acid detection method of the pathogenic mutants;

when the sample contains target DNA and when the target DNA fragment binds to the Cas protein and crRNA in the CRISPR system to form the ternary complex, the trans-cleavage activity of the Cas protein is activated, the Cas protein cleaves the first probe sequence so that when the colloidal gold probe flows to the C tape, the conjugate A binds to the antibody A to produce color, and when the colloidal gold probe flows to the T tape, the conjugate B binds to the antibody B to produce color, thus the result is positive; when there is no target DNA fragment, the ternary complex cannot be formed, thereby not able to activate the trans-cleavage activity of the Cas protein, the colloidal gold probe can only flow to the C tape to bind to the antibody A to produce color, but cannot flow to the T tape, thus the result is negative, thereby realizing the purpose of rapidly detecting and visual reading of the detection result without depending on equipment and instruments so as to really realize the instant detection.

And/or, the instant nucleic acid detection kit includes a Cas protein and a fluorescent probe, the fluorescent probe includes a second probe sequence as well as a fluorophore and a quenching group that are respectively labeled at two ends of the second probe sequence, and is used for combining with the CRISPR process to detecting the sample nucleic acids in the abovementioned instant nucleic acid detection method of the pathogenic mutants, in like manner, if the target DNA fragment is present, the second probe sequence is correspondingly cleaved to emit light, otherwise, light is not emitted. The fluorescent value is detected using ELIASA, so as to correspondingly realize the purpose of detecting the pathogenic mutants.

Specifically, the conjugate A is biotin which is conjugated with streptavidin, the conjugate B is fluorescein isothiocyanate, the antibody A is an anti-streptavidin antibody, the antibody B is an anti-fluorescein isothiocyanate antibody, and the first probe sequence is cleaved. When the colloidal gold probe flows to the C tape, streptavidin conjugated with biotin binds to the anti-streptavidin antibody and is color developed on the C tape; when the colloidal gold probe flows to the T tape, the fluorescein isothiocyanate binds to the anti-fluorescein isothiocyanate antibody to produce color, thus the result is positive; the first probe sequence is not cleaved, the colloidal gold probe can only flow to the C tape to produce color but cannot flow to the T tape and cannot be color developed on the T tape, thus the result is negative; if the colloidal gold probe is not color developed on the C tape, it indicates that the test paper itself has a quality problem, as such, the purposes of rapid detection and visual reading of the detection result are realized.

Specifically, when the pathogen is novel coronavirus, the novel coronavirus includes E gene, S gene 501 site, S gene 478 site and S gene H69-V70 site, the first probe sequence is as shown in SEQ ID NO. 9, the second probe sequence is as shown in SEQ ID NO. 10, the kit also includes a forward RT-RPA primer and a reverse RT-RPA primer, the sequence of the forward RT-RPA primer is as shown in SEQ ID NO. 1, and the sequence of the reverse RT-RPA primer is as shown in SEQ ID NO. 2 and used for detecting the E gene;

and/or, the sequence of the forward RT-RPA primer is as shown in SEQ ID NO. 3, and the sequence of the reverse RT-RPA primer is as shown in SEQ ID NO. 4 and used for detecting the S gene 501 site;

and/or, the sequence of the forward RT-RPA primer is as shown in SEQ ID NO. and the sequence of the reverse RT-RPA primer is as shown in SEQ ID NO. 6 and used for detecting the S gene 478 site;

and/or, the sequence of the forward RT-RPA primer is as shown in SEQ ID NO. 7, and the sequence of the reverse RT-RPA primer is as shown in SEQ ID NO. 8.

Specifically, the kit also includes a crRNA sequence which is crRNA-E for E gene, and the sequence of crRNA-E is as shown in SEQ ID NO. 11;

and/or, the crRNA sequences are crRNA-N501 and crRNA-Y501 for S gene 501 site, the sequence of crRNA-N501 is as shown in SEQ ID NO. 12, and the sequence of crRNA-N501 is as shown in SEQ ID NO. 13;

and/or, the crRNA sequences are crRNA-H69-V70 and crRNA-ΔH69-V70 for S gene H69-V70 site, the sequence of crRNA-H69-V70 is as shown in SEQ ID NO. 14, and the sequence of crRNA-ΔH69-V70 is as shown in SEQ ID NO. 15;

and/or, the crRNA sequences are crRNA-T478 and crRNA-K478 for S gene 478 site, the sequence of crRNA-T478 is as shown in SEQ ID NO. 16, and the sequence of crRNA-K478 is as shown in SEQ ID NO. 17.

By selecting the above detection sites and correspondingly designing crRNA, the purpose of detecting the novel coronavirus (SARS-CoV-2) mutants can be realized.

The technical solution of the present disclosure will be further illustrated in combination with specific examples.

Figure 1B:
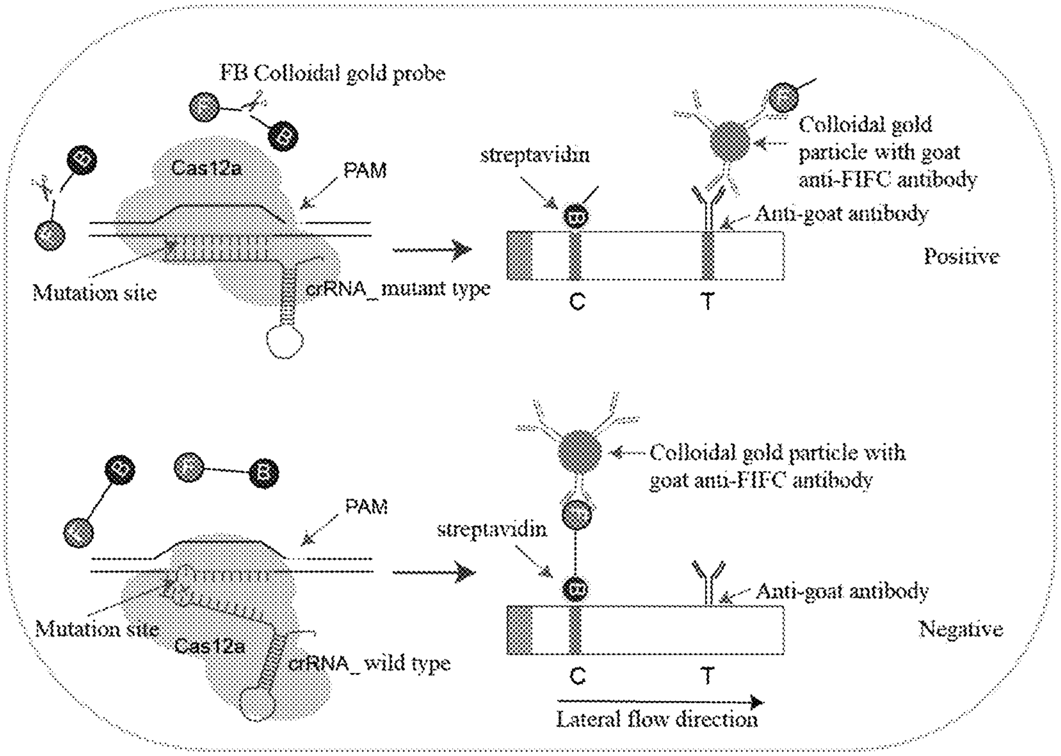
FIG. 1B is a schematic diagram of the colloidal gold test paper method for nucleic acid detection of novel coronavirus mutants.
Figure 1C:
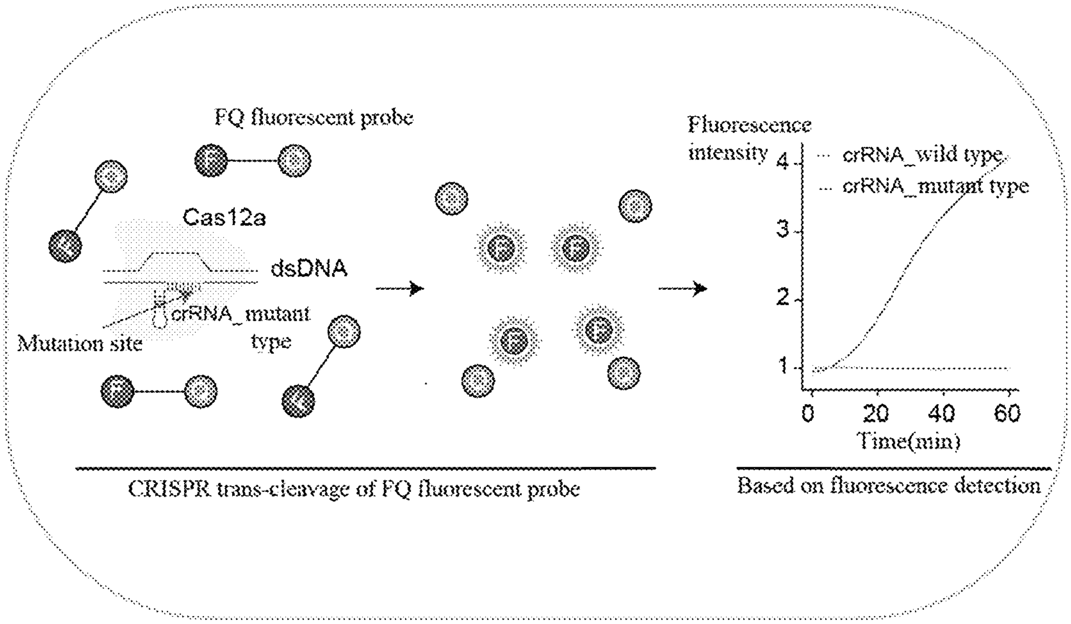
FIG. 1C is a schematic diagram of the fluorescence signal detection method for nucleic acid detection of novel coronavirus mutants.

By taking the detection of novel coronavirus (SARS-CoV-2) mutants as examples, a detection technical routine is seen in FIGS. 1A to 1C, and detailed elaborations are as follows:

Example 1

1) Cleavage and Release of Pathogenic Nucleic Acid

Samples collected from nasopharyngeal swabs or other collected samples were put into a sample lysate to be lysed for 5 min at 37° C., and then RNA in the samples was lysed and released to enter the next RT reaction. The sample lysate was purchased from Shengxiang Biotechnology Co., Ltd.

2) Design and Screening of Optimal RT-RPA Primer Applied to Mutant Detection

Figure 2A:
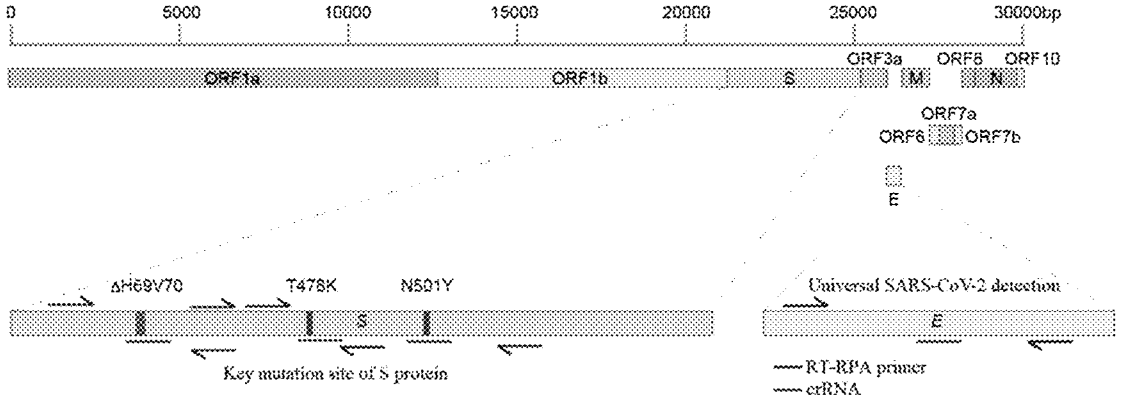
FIG. 2A is a diagram of general detection gene and mutant gene detection sites of SARS-CoV-2 viruses.
Figure 2B:
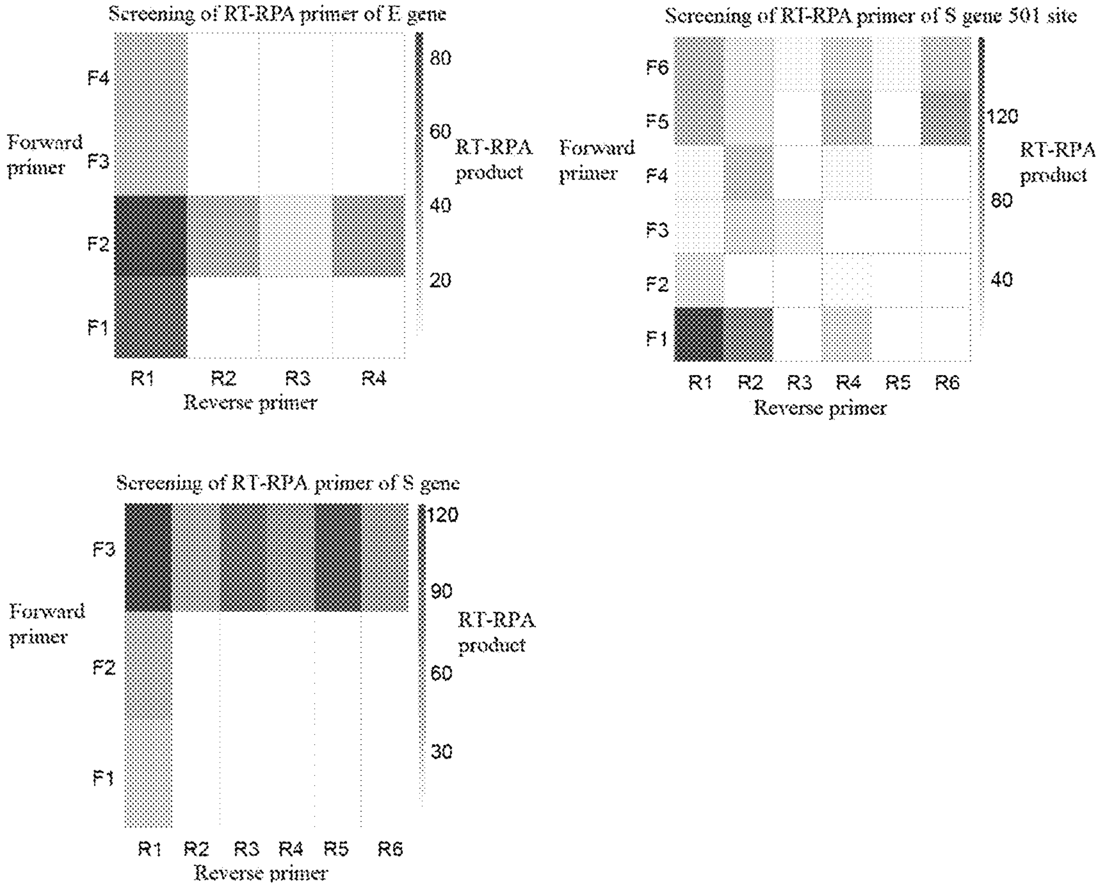
FIG. 2B is an ImageJ quantification graph of agarose electrophoresis measurement value.

The SARS-CoV-2 genome is composed of about 29903 nucleotides, encodes 12 open reading frames, and includes structural protein coding genes such as spike (S), nucleocapsid (N), membrane (M) and envelope (E). This example selected E gene and S gene in the SARS-CoV-2 genome as detection sites, wherein the E gene was used as a universal detection target of SARS-CoV-2. The SARS-CoV-2 genome was significantly mutated for several times during the propagation, and the key amino acid mutation in S gene was generally used for genetic typing of SARS-CoV-2 mutant strains. Therefore, 501 and 478 sites of S gene were selected as SARS-CoV-2 mutants for detection (FIG. 2A: arrows represent forward and reverse RT-RPA primers for virus detection, and a short line represents crRNA binding site). DNA obtained by reverse transcription was estimated by agarose gel electrophoresis assay, the optimal RT-RPA primer pairs was screened by amplification product of RPA reaction, and quantification was performed by using ImageJ (FIG. 2B). Finally, three pairs of RT-RPA primers were selected, including ERPAF2 (SEQ ID NO. 1: gaagagacaggtacgttaatagttaatagc)/ERPAR1 (SEQ ID NO. 2: cagatttttaacacgagagtaaacgtaaaaagaa), S501RPAF1 (SEQ ID NO. 3: tgtatagattgtttaggaagtctaatctcaa)//S501RPAR1 (SEQ ID NO. 4: agactcagtaagaacacctgtgcctgttaa)/and S478RPAF3 (SEQ ID NO. 5: accagatgattttacaggctgcgttatagcttg)//S478RPAR5 (SEQ ID NO. 6: caattaaaacctttaacaccattacaa), which were respectively used as optimal primers of E gene and 501 and 478 sites of S gene.

3) Recombinase Polymerase Amplification Technology (RT-RPA)

First, RNA extracted from the sample was added into 20 μL of premix solution to be incubated for 15 min at 37° C. to complete reverse transcription reaction (RT reaction), so that RNA extracted from the example was converted into cDNA. Where, the formula of the premix solution is seen in Table 1.

After reverse transcription reaction was completed, cDNA was amplified by recombinase polymerase (RPA). Specific steps were as follows: cDNA was added into a RPA amplification reaction system to be incubated for 15 min at 37° C. to complete RPA reaction, so as to realize amplification and enlargement of signals. The formula of the above system is seen in Table 2.

Reverse transcription kit RNase H and T4 gene 32 protein were purchased from New England Biolabs™, and RevertAid Reverse Transcriptase™ was purchased from Thermo Scientific. RPA kit TwistAmp Basic Kit was purchased from TwistDX™.

TABLE 2

| Reagent | Volume (μL) |
|---|---|
| Formula of premix solution of reverse transcription reaction system | |
| 5× RT buffer | 4.0 |
| Forward primer (50 μM) | 0.5 |
| Reverse primer (50 μM) | 0.5 |
| dNTPs (10 mM) | 2.0 |
| RNase inhibitor (20 U) | 0.5 |
| Reverse transcriptase (200 U) | 1.0 |
| RNase H (500U) | 0.4 |
| T4 gene 32 protein (10 mg/mL) | 1.1 |
| RNA template | 10 |
| RNA-free water | Add to 20 |
| Formula of RPA amplification reaction system | |
| Twist buffer | 29.5 |
| Forward primer (10 μM) | 2.4 |
| Reverse primer (10 μM) | 2.4 |
| RNA-free water | 3.2 |
| Mix the above solutions, and add the mixed solution into TwistAmp RPA vacuum freeze-dried powder | |
| cDNA reaction product | 10 |
| MgAcO (280 mM) | 2.5 |

3) Combined Detection of CRISPR-Cas12a Process and Colloidal Gold Test Paper Method A colloidal gold reaction system based on CRISPR-Cas12a process was prepared according to Table 3, evenly mixed and then incubated for 30 min at 37° C. 10 μL of prepared colloidal gold reaction system was applied to a sample pad of a colloidal gold test paper strip, the test paper strip was quickly immersed into a tube containing 80 μL of test paper strip buffer solution, and results were read after developing for 2-3 min. a colloidal gold probe was purchased from Nanjing Zhongding Biotechnology Co., Ltd, and the colloidal gold test paper strip was purchased from Milenia Biotec.

TABLE 3

Colloidal gold reaction system based on CRISPR-Cas12a process

| Reagent | Volume (μL) |
|---|---|
| 10× buffer | 10 |
| Cas12a (10 μM) | 2 |
| RPA product | 5 |
| crRNA (60 μM) | 1 |
| $MgCl_2$ (1M) | 1 |
| FB colloidal gold (2.5 μM) | 10 |
| RNA-free water | Add to 100 μL |

Note:
FB colloidal gold probe sequence (first probe sequence) is SEQ ID NO. 9: gattagcgtacgcacgttac Example 2

The difference from example 1 is that 3), a fluorescence detection system based on CRISPR-Cas12a process was prepared, as shown in Table 4, the system was sufficiently and evenly mixed and then added into a 96-well plate and placed in a ELIASA for constant-temperature reaction at 37° C., and the fluorescence value was measured every 30 s for 60 min. Exciting light and emitting light from ELIASA were respectively 480 nm and 520 nm. EnGen® Lba Cas12a (Cpf1) and buffer liquid system were purchased from New England Biolabs® to be used for CRISPR-Cas12a reaction in this example of the present disclosure. crRNA was obtained by in-vitro transcription.

TABLE 4

Fluorescence detection system based on CRISPR-Cas12a process

| Reagent | Volume (μL) |
|---|---|
| 10× buffer | 10 |
| Cas12a (10 μM) | 2 |
| RPA product | 5 |
| crRNA (60 μM) | 1 |
| FQ fluorescence probe (1 μM) | 2.5 |
| $MgCl_2$ (1M) | 1 |
| RNA-free water | Add to 100 μL |

Figure 3A:
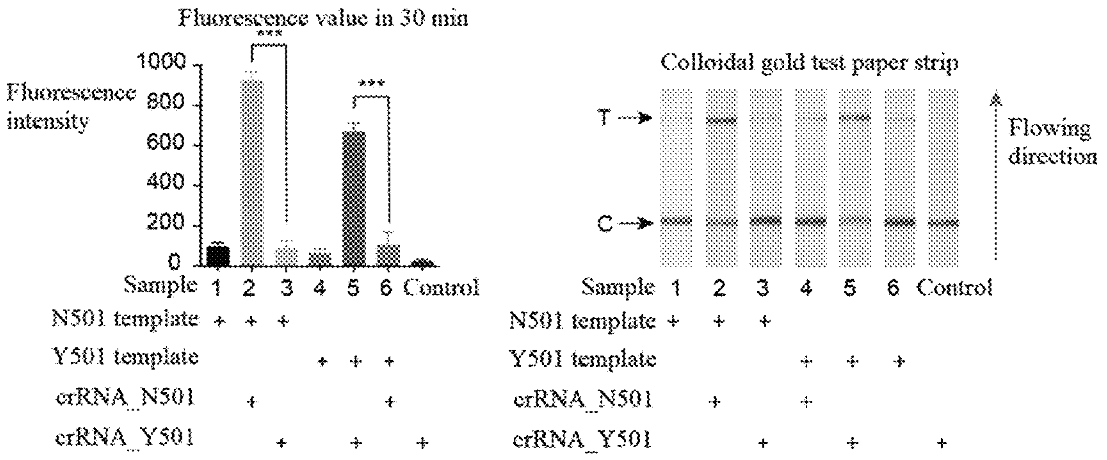
FIG. 3A is a fluorescence value detection bar graph and colloidal gold test paper graph for detecting specificity of S gene 501 site of SARS-CoV-2.
Figure 3B:
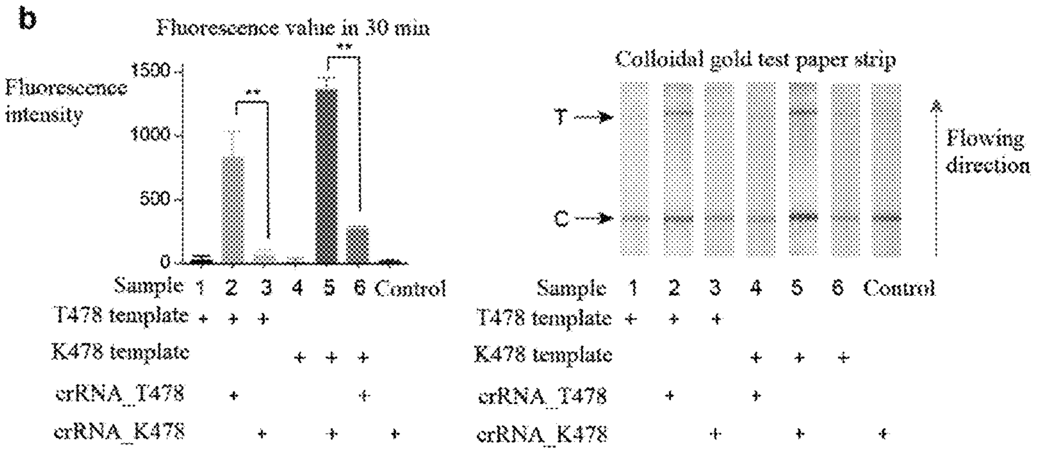
FIG. 3B is a fluorescence value detection bar graph and colloidal gold test paper graph for detecting specificity of S gene 478 site of SARS-CoV-2.
Figure 3C:
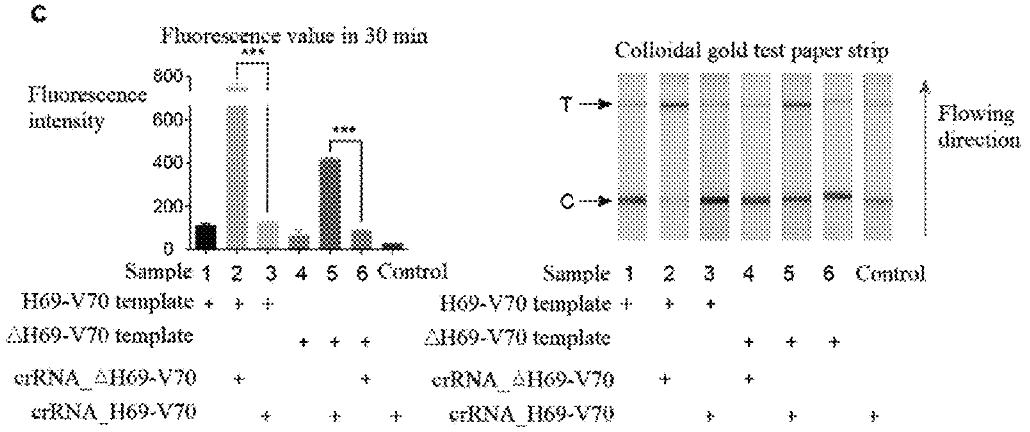
FIG. 3C is a fluorescence value detection bar graph and colloidal gold test paper graph for detecting specificity of S gene H69-V70 site of SARS-CoV-2.

Note:
FQ fluorescence probe sequence (second probe sequence) is SEQ ID NO10: gctaatcg I. Estimation of Specificity of this Method for Detection of SARS-CoV-2 Mutants To detect the specificity of this method on SARS-CoV-2 mutants, crRNAs including crRNA-N501 (SEQ ID NO. 12: aauuucuacu guuguagaucaacccacuaauggugu) and crRNA-Y501 (SEQ ID NO. 13: aauuucuacu guuguagau caacccac-uuauggugu) for SARS-CoV-2 S gene 501 site, crRNA-H69-V70 (SEQ ID NO. 14: aauuucuacu guuguagau cuauacaugucucuggg) and crRNA-ΔH69-V70 (SEQ ID NO. 15: aauuucuacu guuguagau cuaucucugggaccaau) for SARS-CoV-2 S gene H69-V70 site and crRNA-T478 (SEQ ID NO. 16: aauuucuacu guuguagau ugugguaauguuccaca) and crRNA-K478 (SEQ ID NO. 17: aauuucuacu guuguagau ugugguaauguuccaaa) for SARS-CoV-2 S gene 478 site, and primers for SARS-CoV-2 S gene H69-V70 site being S6970RPAF (SEQ ID NO. 7: tttccaatgttacttggttccatgtttac-tat)/S6970RPAR (SEQ ID NO. 8: ttaacaataagtagggactgggtcttcgaatc) were designed, SARS-CoV-2 pseudovirus and mutated pseudoviruses such as ΔH69-V70, N501Y and T478K contained in SARS-CoV-2 were respectively measured by the designed crRNA and utilizing the above screened RT-RPA primer, double-stranded dsDNA of the above viruses from the above genes were incubated respectively with Cas12a nuclease, a FQ fluorescence probe and separate crRNA at 37° C., and fluorescence values were measured in 30 min. The results are respectively seen in FIG. 3A (left figure), FIG. 3B (left figure) and FIG. 3C (left figure), and an error bar is mean±SD. * represents t-test detection $P<0.005$, and  represents t-test detection $P<0.01$, wherein RNAase-free water is used as negative control, C is a control line, and T is a detection line. Similarly, colloidal gold test paper was used for specificity analysis of the above template. The results are respectively seen in FIG. 3A (right figure), FIG. 3B (right figure) and FIG. 3C (right figure). It can be seen from fluorescence detection or colloidal gold test paper strip results of FIG. 3A, FIG. 3B and FIG. 3C that the present disclosure can easily distinguish mutation in S protein, including firstly reported N501Y (FIG. 3A) of Beta pedigree and recently reported Delta as well as T478K (FIG. 3B) of Omicron pedigree. In addition, it also can distinguish small deletions on S gene, for example ΔH69-V70 (FIG. 3C) of Alpha and Omicron pedigree.

II. Estimation of Sensitivity of this Method for Detection of SARS-CoV-2 Mutants The sensitivity of T478, K478, N501 and Y501 of E gene and S gene of SARS-CoV-2 were respectively detected by using $10^7$, $10^6$, $10^5$, $10^4$, $10^3$, $10^2$, 10 and 5 pseudovirus copy number gradients, the designed crRNA for SARS-CoV-2 E gene was crRNA-E (SEQ ID NO. 11: aauuucuacuguuguagaucaagacucacguuaacaa). Double-stranded dsDNA from the above gene in pseudoviruses together with Cas12a, probes and crRNA was incubated at 37° C. The results are respectively shown in FIG. 4A, FIG. 4B, FIG. 4C, FIG. 4D and FIG. 4E. The fluorescence intensity (F30/F0) represents a ratio of a fluorescence value in 30 min to a starting fluorescence value in 0 min (left figure), and the colloidal gold results are presented in right figure, wherein RNAase-free water is used as negative control, C is the control line, and T is the detection line.

Figure 4A:
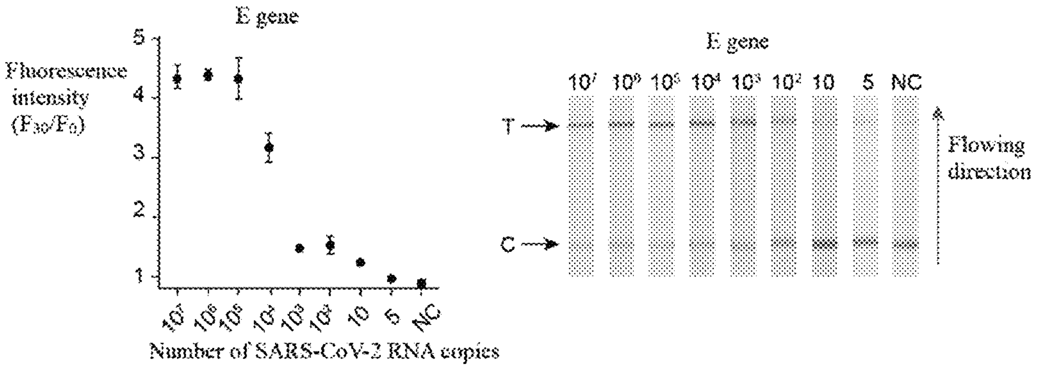
FIG. 4A is a fluorescence value detection scatter diagram and colloidal gold test paper graph for detecting sensitivity of E gene of SARS-CoV-2.
Figure 4B:
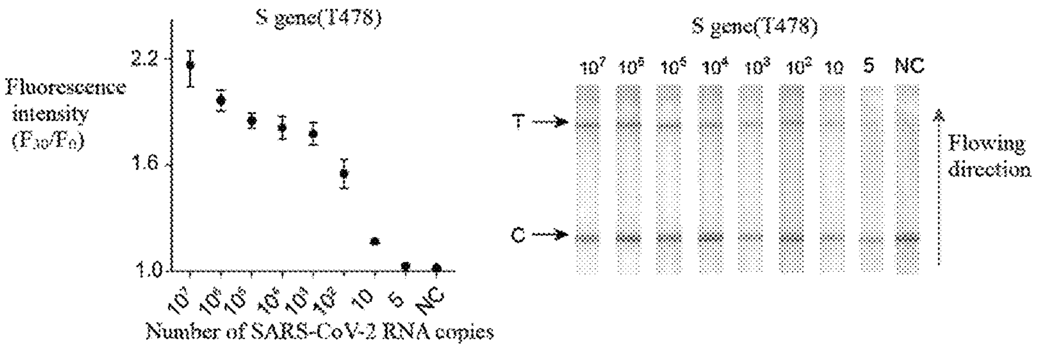
FIG. 4B is a fluorescence value detection scatter diagram and colloidal gold test paper graph for detecting sensitivity of T478 of S gene of SARS-CoV-2.
Figure 4C:
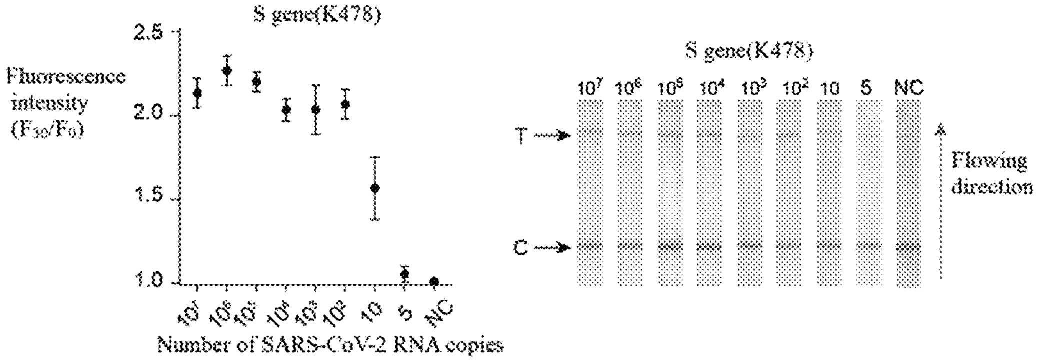
FIG. 4C is a fluorescence value detection scatter diagram and colloidal gold test paper graph for detecting sensitivity of K478 of S gene of SARS-CoV-2.
Figure 4D:
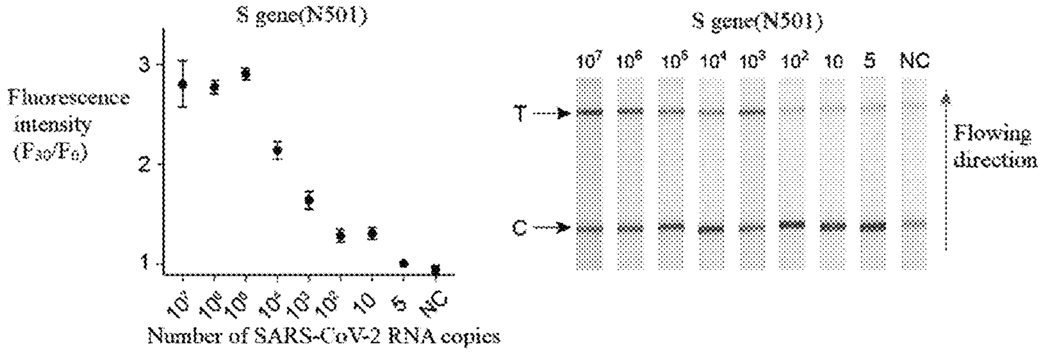
FIG. 4D is a fluorescence value detection scatter diagram and colloidal gold test paper graph for detecting sensitivity of N501 of S gene of SARS-CoV-2.
Figure 4E:
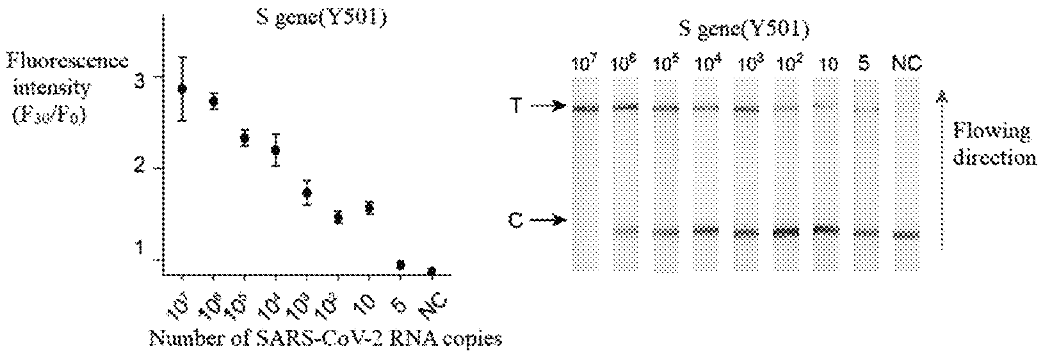
FIG. 4E is a fluorescence value detection scatter diagram and colloidal gold test paper graph for detecting sensitivity of Y501 of S gene of SARS-CoV-2.

Based on fluorescence reads, the results show that the detection lines of all the target regions (E gene, N501, Y501, T478 and K478) are about 10 copies, which is equivalent to a fact that the Ct value of RT-qPCR is 35. The fluorescence result in 30 min shows the detection sensitivity of N501 is slightly higher than that of Y501 (FIG. 4D and FIG. 4E), while the detection sensitivity of T478 is slightly lower than that of K478 (FIG. 4B and FIG. 4C). When the colloidal gold reads are used, the detection of Y501 and K478 is the most sensitive, and the detection limit of each reaction is about 10 copies (FIG. 4E and FIG. 4C).

III. Estimation of Detection Ability of this Method on Clinical Sample Mutants

Figure 5A:
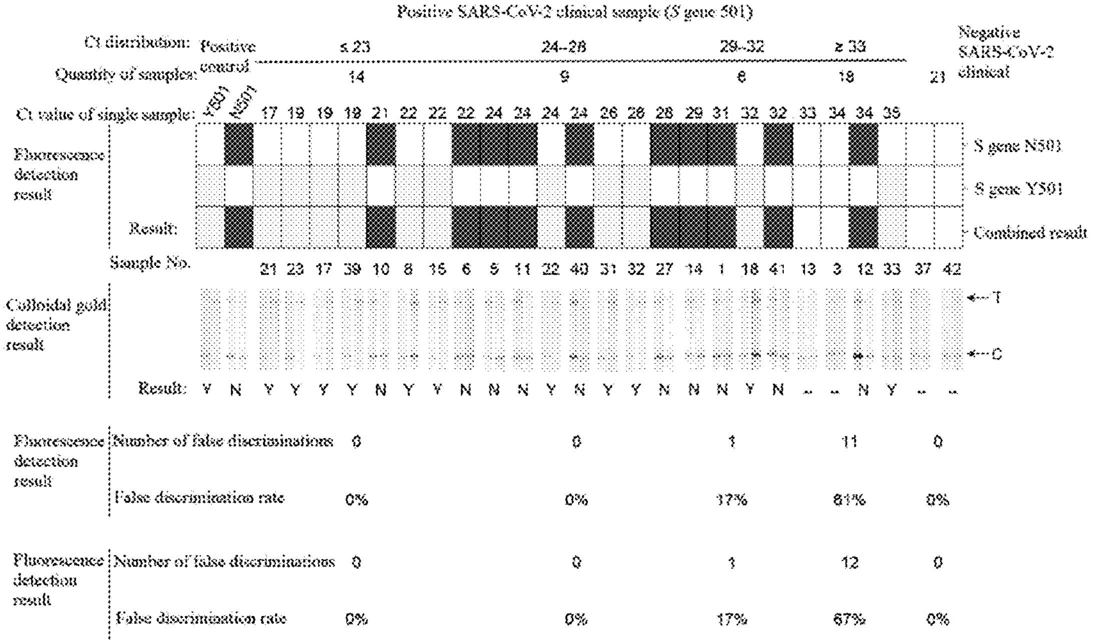
FIG. 5A is a summary graph of detection performances of S gene 501 sites in 68 clinical samples.

To estimate the detection performance of this method in the aspect of recognizing SARS-CoV-2 mutants, the 501 and 478 sites of S gene were detected. N501Y was used as common mutation sites of Alpha, Beta, Gamma, Omicron and other mutants, and 68 clinical samples were collected and underwent mutant detection. The results are seen in FIG. 5A. Distinguishing was conducted according to the Ct value of the SARS-CoV-2 positive sample, the total number of clinical samples in each Ct region is shown on the top, 47 positive samples (the Ct value is between 13 and 35) and 21 negative samples are detected, the dark color represents fluorescence read-based positive results detected by using crRNA-N501, the light color represents fluorescence read-based results detected by using crRNA-Y501, and white color represents negative results. In addition, colloidal gold results obtained by using crRNA-N501 (left) and crRNA-Y501 (right) are shown in the middle of the figure, wherein N, N501; Y, Y501; –, negative result or no detection, and the false discrimination number and false discrimination rate of each CT region are shown at the bottom. It is identified by genomic sequencing that among 68 clinical samples, 28 are N501 samples, 19 are Y501 samples.

The results show that all the mutants can be distinguished from samples of $Ct<32$ through colloidal gold reads or fluorescence reads (FIG. 5A), however, when the detection Ct value of the sample exceeds 33, the distinguishing ability of this method is significantly reduced, which may be limited by the sensitivity of S gene 501 site.

Figure 5B:
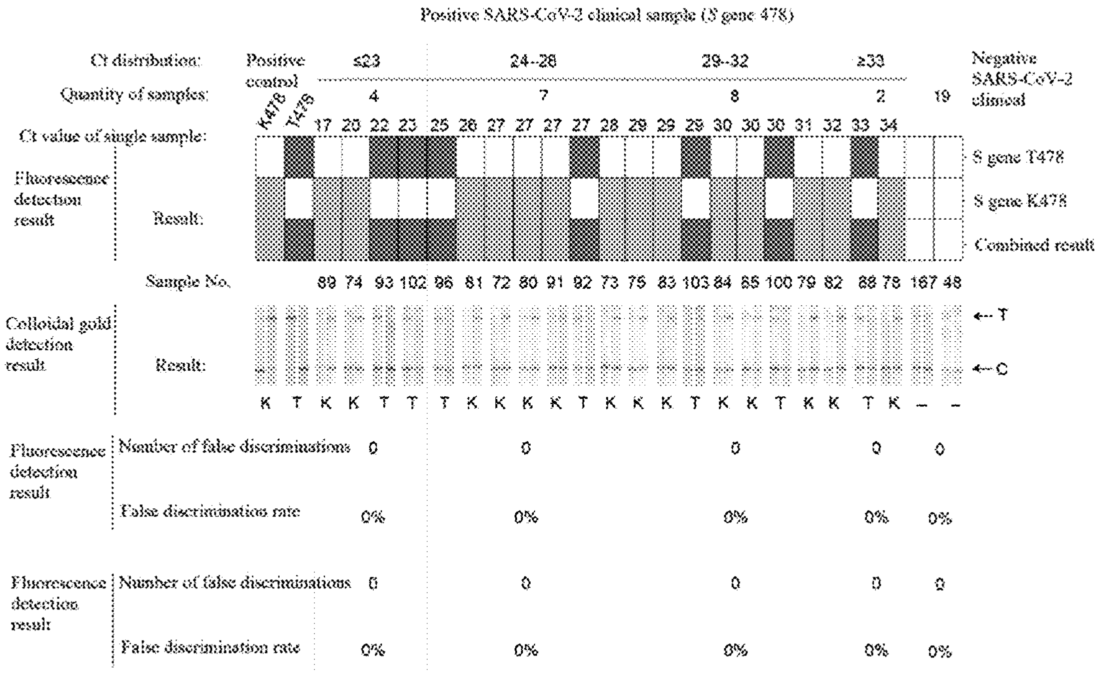
FIG. 5B is a summary graph of detection performances of S gene 478 sites in 40 clinical positive samples.

The S gene 478 site can be used as an important target for identifying Delta and Omicron pedigrees, 40 clinical positive samples are totally collected and undergo mutant detection, results are seen in FIG. 5B, 21 positive samples (a Cr range is 17-34) and 19 negative samples are detected, the dark color represents fluorescence read-based positive results detected by using crRNA-N501, and the light color represents fluorescence read-based positive results detected by using crRNA-Y501. White color represents negative results. Colloidal gold results obtained by using crRNA-T478 (left) and crRNA-K478 (right) are shown in the middle of the figure, wherein T, T478; K, K478; –, negative result or no detection. SARS-CoV-2 pseudovirus RNA is used as positive control. It is identified by genomic sequencing that 7 T478 samples and 14 K478 samples are included. The results show 478 sites of all target S genes can be distinguished (FIG. 5B). These clinical data indicate that the present disclosure can accurately and sensitively detect and distinguish SARS-CoV-2 mutants.

The above descriptions are only preferred embodiments of the present disclosure but not used for limiting the present disclosure. Any amendments, equivalent replacements and improvements made within the principle of the present disclosure should be included within the protective scope of the present disclosure.

What is claimed is:

1. An instant nucleic acid detection kit for pathogenic mutants, comprising:

a Cas protein, colloidal gold test paper and a colloidal gold probe, wherein the colloidal gold test paper comprises a C tape and a T tape, the colloidal gold probe comprises a first probe sequence as well as a conjugate A and a conjugate B that are respectively connected with two ends of the first probe sequence, wherein the first probe sequence is SEQ ID NO. 9, the C tape is provided with an antibody A binding to the conjugate A, and the T tape is provided with an antibody B binding to the conjugate B, the colloidal gold probe is used for combining a CRISPR process with a colloidal gold test paper method for detecting the sample nucleic acids of the pathogenic mutants.

2. The instant nucleic acid detection kit of claim 1, wherein the conjugate A is a biotin which is conjugated with streptavidin, the conjugate B is a fluorescein isothiocyanate, the antibody A is an anti-streptavidin antibody, and the antibody B is an anti-fluorescein isothiocyanate antibody.

3. The instant nucleic acid detection kit of claim 2, wherein when a pathogen is novel coronavirus, the novel coronavirus comprises E gene, S gene 501 site, S gene 478 site and S gene H69-V70 site, the second probe sequence is SEQ ID NO. 10, the kit also comprises a forward RT-RPA primer and a reverse RT-RPA primer, wherein the forward RT-RPA primer is SEQ ID NO. 1, and the reverse RT-RPA primer is SEQ ID NO. 2 and used for detecting the E gene.

4. The instant nucleic acid detection kit for pathogenic mutants of claim 2, wherein the forward RT-RPA primer is SEQ ID NO. 3, and the reverse RT-RPA primer is SEQ ID NO. 4 and used for detecting the S gene 501 site.

5. The instant nucleic acid detection kit of claim 2, wherein the forward RT-RPA primer is SEQ ID NO. 5, and the reverse RT-RPA primer is SEQ ID NO. 6 and used for detecting the S gene 478 site.

6. The instant nucleic acid detection kit of claim 2, wherein the sequence of the forward RT-RPA primer is as shown in SEQ ID NO. 7, and the sequence of the reverse RT-RPA primer is as shown in SEQ ID NO. 8.

7. The instant nucleic acid detection kit of claim 1, wherein the instant nucleic acid detection kit also comprises a crRNA sequence which is crRNA-E for E gene, and the sequence of crRNA-E is as shown in SEQ ID NO. 11.

8. The instant nucleic acid detection kit of claim 1, wherein the crRNA sequences are crRNA-N501 and crRNA-Y501 for S gene 501 site, the sequence of crRNA-N501 is SEQ ID NO. 12, and the sequence of crRNA-N501 is SEQ ID NO. 13.

9. The instant nucleic acid detection kit of claim 1, wherein the crRNA sequences are crRNA-H69-V70 and crRNA-ΔH69-V70 for S gene H69-V70 site, the sequence of crRNA-H69-V70 is SEQ ID NO. 14, and the sequence of crRNA-ΔH69-V70 is SEQ ID NO. 15.

10. The instant nucleic acid detection kit of claim 1, wherein the crRNA sequences are crRNA-T478 and crRNA-K478 for S gene 478 site, the sequence of crRNA-T478 is SEQ ID NO. 16, and the sequence of crRNA-K478 is SEQ ID NO. 17.

* * * * *